(12) United States Patent
Bakonyl et al.

(10) Patent No.: US 6,670,486 B1
(45) Date of Patent: Dec. 30, 2003

(54) PROCESS FOR RACEMIZATION

(75) Inventors: Mária Bakonyl, Budapest (HU); Tiborné Bai, Budapest (HU); Zsolt Dombrády, Budapest (HU); Katalin Gáspár, Göd (HU); Attila Supic, Budapest (HU)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/830,930

(22) PCT Filed: Nov. 5, 1999

(86) PCT No.: PCT/HU99/00076

§ 371 (c)(1),
(2), (4) Date: Jun. 18, 2001

(87) PCT Pub. No.: WO00/27840

PCT Pub. Date: May 18, 2000

(30) Foreign Application Priority Data

Nov. 9, 1998 (HU) .............................................. 9802586

(51) Int. Cl.⁷ .............................................. C07D 333/22
(52) U.S. Cl. ............................................ 549/76; 549/77
(58) Field of Search ..................................... 549/76, 77

(56) References Cited

U.S. PATENT DOCUMENTS 3,632,646 A * 1/1972 Hageman et al. ........... 260/559
4,364,958 A * 12/1982 Seres et al. .................. 548/544
4,769,486 A    9/1988 Harada et al.
5,204,469 A    4/1993 Descamps et al.

FOREIGN PATENT DOCUMENTS

| EP | 466 569  | 1/1992  |
| WO | 98/51681 | 11/1998 |
| WO | 98/51682 | 11/1998 |
| WO | 98/51689 | 11/1998 |

OTHER PUBLICATIONS

Alabaster R.J., et al., Tetrahedron: Asymmetry, (1997), vol. 8, No. 3, pp. 447–450.
Derwent Abstract, XP–002134523.

* cited by examiner

Primary Examiner—Joseph K. McKane
Assistant Examiner—Kamal Saeed
(74) Attorney, Agent, or Firm—Paul E. Dupont; Michael D. Alexander

(57) ABSTRACT

The invention relates to the racemisation process of the optically active [2-(2-thienyl)ethylamino](2-halogenophenyl)acetamides of general formula (VII) by using basic compounds.

Figure 1:
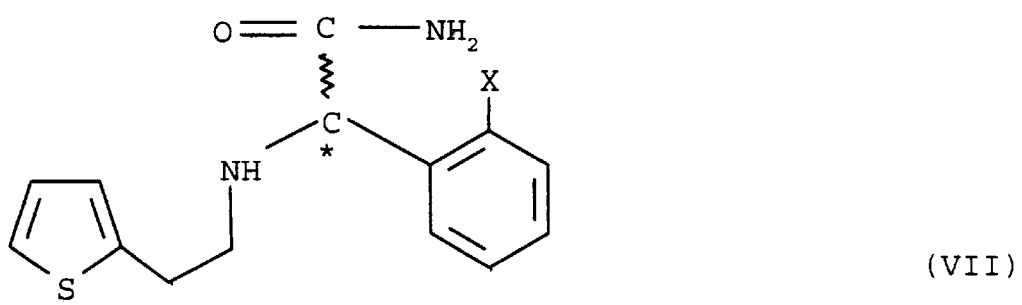
Figure 2:
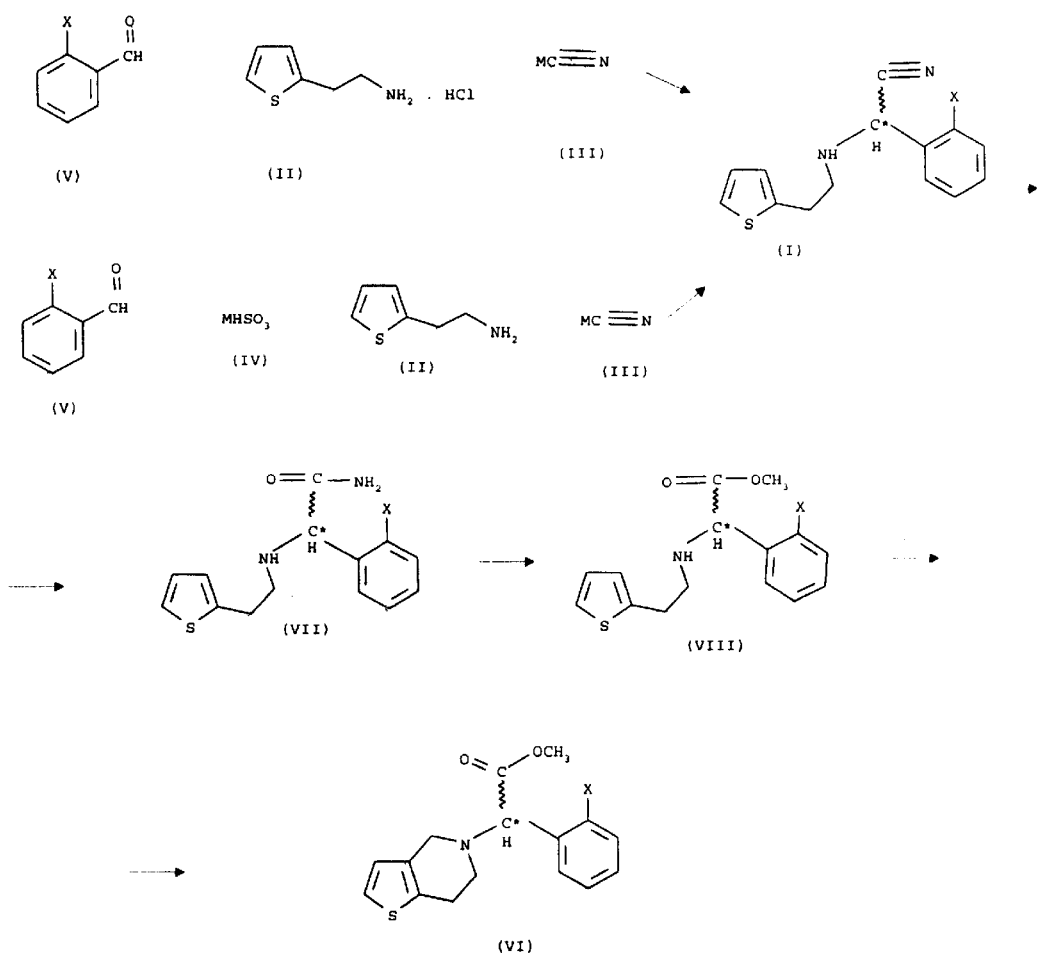

The resulting racemic compounds of general formula (VII) can thus be recycled into synthesis of the therapeutically useful compounds of general formula (VI).

10 Claims, 2 Drawing Sheets

(VII)

1. Reaction scheme

PROCESS FOR RACEMIZATION

This invention relates to the novel process for the preparation of the racemic intermediates of formula (VII) wherein x is halogen.

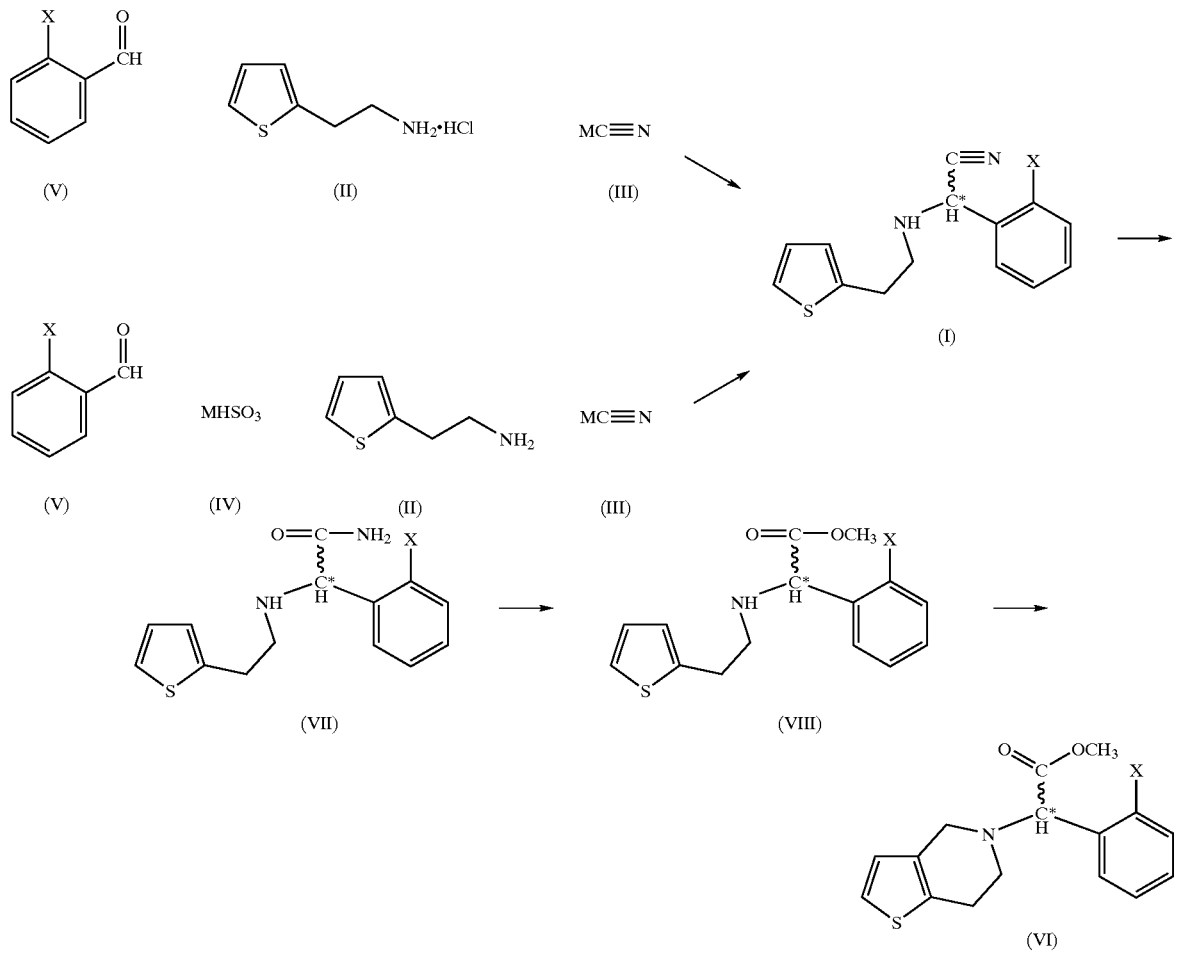

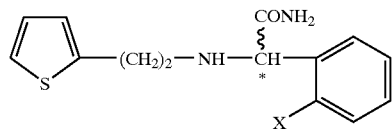

(VII)

It is known that methyl (2-halogenophenyl)(6,7-dihydro-4H-thieno[3,2-c]pyridin-5-yl)acetates and their salts can advantageously be used in the therapy, first of all owing to their platelet-aggregation-inhibitory and antithrombotic effects. A particularly favourable representative of these compounds, falling under the general formula (VI)—wherein X means chloro atom-, is the dextrorotatory methyl (+)-[(S)-(2-chlorophenyl)-(6,7-dihydro-4H-thieno[3,2-c] pyridin-5-yl)acetate hydrogen sulfate], designated with the international non-propriety name (INN) clopidogrel (European patent application Publication Nr. 099802).

PCT application Nos. PCT/HU98/00046, PCT/HU98/00047 and PCT/HU98/00048 (WO 98/51682, WO 98/51681 and WO 98/51689 respectively), which are incorporated herein by reference, describe the novel synthesis of the compounds of formula (VI) as shown in the following scheme.

In the course of that synthesis, when the dextrorotatory isomers of the compounds of formula (VII) are further transformed, the levorotatory isomers of the compounds of formula (VII) form waste and cause considerable loss.

Our aim was to solve the racemization of the optically active compounds of general formula (VII) which are not used further in the synthesis and which are of different optical purity, ensuring thus the recycling of the not used isomer into the synthesis process.

We have found that the individual optically active compounds of general formula (VII) or their acid addition salts can be transformed into the racemic compounds of general formula (VII) on the effect of treating them with basic inorganic or organic compounds. Racemisation of mixtures consisting of various ratio of the levorotatory and dextrorotatory isomers of compounds of general formula (VII) can also be solved in this way. In the course of the process, as for inorganic base an alkali metal hydroxide, as for organic base an alkali metal alcoholate can favourably be used. Such are for instance, sodium hydroxide, potassium hydroxide, and sodium ethylate or methylate, potassium ethylate or methylate. The process can be performed in water-miscible or water-non-miscible organic solvents, as well as in the mixture of an organic solvent and water. Favourable solvents are methanol, ethanol, isopropanol, benzene and toluene.

The reaction is usually performed at a temperature between +20° C. and +100° C., favourably between +40° C. and +60° C.

As for starting material, optional acid addition salts of the levorotatory or dextrorotatory compounds of general formula (VII) can be used, favourable salts are tartarate and hydrochloride salts.

The amount of the base is favourably 5–500 mol %, counted for the amount of the optically active compound to be racemized, taking into consideration that when starting from an acid addition salt, a part of the base will be used for the liberation of the compound of general formula (VII).

Further details of the invention are demonstrated by the following examples, without limiting our claims to the content of the examples

EXAMPLES

Examples Demonstrating: The Preparation of the Optically Active Levorotatory Compounds of General Formula (VII) to be Racemized, Furthermore the Preparation of the Optically Active Dextrorotatory Compounds of General Formula (VII), and Their use in the Synthesis of the Compounds of General Formula (VI)

Example 1

[2-(2-Thienyl)ethylamino](2-chlorophenyl)acetonitrile 104 g (1 mol) of sodium bisulfite is dissolved in the mixture of 900 ml of water and 250 ml of ethanol and to the solution 140,6 g (1 mol) o-chlorobenzaldehyde is added. After a few minutes the aldehyde bisulfite adduct precipitates in the form of white crystals, while the temperature raises to 40° C. After 1 hour of stirring 127,2 g (1 mol) of 2-(2-thienyl)ethylamine is added to the reaction mixture, then it was stirred at 50° C. for 2 hours. During this time the crystalline aldehyde bisulfite transforms into an oily material. The mixture is cooled to room temperature and the solution of 49 g (1 mol) of sodium cyanide in 100 ml of water is added to it. During the addition the temperature of the reaction mixture raises to 40° C. The mixture is then stirred at 60° C. till the reaction is completed (1 hour). The oily organic phase is then extracted with 400 ml of 1,2-dichloroethane, washed to cyanide-free with 2×200 ml of water, traces of 2-(2-thienyl)ethylamine are removed by treatment with 100 ml of 3% hydrochloric acid solution. The dichloroethane phase was dried over anhydrous sodium sulfate and evaporated in vacuo. The residual fast crystallizing oil is the product. Weight: 260 g (94%) mp.: 40–41° C. The product was identified by elementary analysis, IR spectrum and $^1$H-NMR investigation.

Example 2

[2-(2-Thienyl)ethylamino](2-chlorophenyl)acetonitrile 9,8 g (0,2 mol) of sodium cyanide is dissolved in 70 ml of water and to the solution first 32,8 g (0,2 mol) of 2-(2-thienyl)ethylamine hydrochloride, then in a period of a few minutes, the solution of 28,2 g (0,2 mol) of o-chlorobenzaldehyde in 30 ml of ethanol are added. During the addition the temperature of the mixture raises to 45° C. The reaction mixture is then stirred at 60° C. for 2 hours, then cooled to room temperature and diluted with 50 ml of water. The resulting oily product is extracted with 100 ml of 1,2-dichloroethane, the organic phase is washed to cyanide-free with 2×50 ml of water, the traces of 2-(2-thienyl) ethylamine are removed by treatment with 20 ml of 3% hydrochloric acid solution. The residual fast crystallizing oil is the product. Weight: 52 g (94%) mp.: 40–41° C. The product was identified as written in Example 1. Quality of the product is identical to that of the product prepared according to Example 1.

Example 3

[2-(2-Thienyl)ethylamino](2-chlorophenyl)acetonitrile Hydrochloride 276,7 g (1 mol) of [2-(2-thienyl)ethylamino](2-chlorophenyl)acetonitrile, prepared according to example 1. or 2., is dissolved in 600 ml of ethanol, to the solution 600 ml of 10% aqueous hydrochloric acid solution is added. Within a few minutes white crystals precipitate, they are collected, washed with 60 ml of 1:1 mixture of 10% hydrochloric acid and ethanol, then with acetone, and they are dried. Weight: 305 g (97,4%), mp.: 153–154° C. The product was identified by elementary analysis, IR spectrum and $^1$H-NMR investigation.

Example 4

[2-(2-Thienyl)ethylamino](2-chlorophenyl)acetonitrile Hydrobromide 13,8 g (0,05 mol) of [2-(2-thienyl)ethylamino](2-chlorophenyl)acetonitrile, prepared according to example 1. or 2., is dissolved in 30 ml of ethanol, to the solution 40 ml of 20% aqueous hydrogen bromide solution is added. The product which precipitates within a few minutes is collected, washed with ethyl acetate and then they are dried. Weight: 14 g (78,2%), mp.: 144–145° C. The product was identified by elementary analysis, IR spectrum and $^1$H-NMR investigation.

Example 5

[2-(2-Thienyl)ethylamino](2-chlorophenyl)acetamide Hydrochloride

Into 1200 ml of methyl acetate 204 g (5.6 mol) of hydrogen chloride gas is introduced at 15–25° C., and to the solution are added 221.4 g (0.8 mol) of the [2-(2-thienyl) ethylamino](2-chorophenyl)acetonitrile, prepared as described in Example 1., and 48 ml (1.2 mol) of methanol. The mixture is stirred at 20–25° C. for 6 hours. In the course of the reaction first the hydrochloride of the starting "nitrile", then gradually the hydrochloride of the resulting "acid amide" precipitates, in the form of white crystals. The crystals are collected by filtration, washed with methyl acetate and dried. Weight: 249 g (94%) mp.: 231–232° C.

The product was identified by elementary analysis, IR spectrum and $^1$H-NMR investigation.

Example 6

[2-(2-Thienyl)etylamino](2-chlorophenyl)acetamide Hydrochloride

Into 700 ml of ethyl acetate at 0–10° C. 109.8 g (3 mol) of hydrogen chloride gas is introduced and to the solution 83 g (0.3 mol) of the [2-(2-thienyl)ethylamino](2-chorophenyl) acetonitrile of formula (I), prepared according to Example 1. or 2., and 15 ml (0.37 mol) of methanol are added and the mixture is slowly, in a period of 20 minutes, heated to 45–50° C. The reaction mixture is then stirred at 45–50° C. for 4 hours, the crystalline product is filtered off at room temperature, washed with ethyl acetate and dried. Weight: 90.4 g (91%) op.: 231–232° C. The quality of the product is identical to that of the product of Example 5.

Example 7

[2-(2-Thienyl)ethylamino](2-chlorophenyl)acetamide 24.8 g (0.075 mol) of [2-(2-thienyl)ethylamino](2-chlorophenyl)acetamide hydrochloride, prepared according to example 5. or 6., is mixed with 170 ml of water, then under mild cooling 30 ml of 10% sodium hydroxide solution and 170 ml of 1,2-dichloroethane are added. The phases are separated, the aqueous phase is extracted with 2×20 ml of 1,2-dichloroethane, the combined organic layer is evaporated in vacuo. Residue: 22 g, fast crystallizing oil. The crude product is recrystallized from 80 ml of isopropyl acetate to give 19,5 g of the crystalline base of formula (VII). Yield: 88,2%, mp.: 90–92° C.

The product was identified by elementary analysis, IR spectrum and $^1$H-NMR investigation.

Example 8
Dextrorotatory [2-(2-Thienyl)ethylamino](2-chlorophenyl) acetamide 38 g (0.129 mol) of racemic [2-(2-thienyl)ethylamino](2-chlorophenyl)acetamide is dissolved at 50° C. in 380 ml of isopropanol containing 2% of water and to this solution is added the 50° C. solution of 10,6 g (0.071 mol) of L(+)-tartaric acid in 230 ml of isopropanol, containing 2% of water. The mixture is stirred at 50° C. for 30 minutes. Thick, white precipitate is formed. To the mixture 3.4 ml (0.09 mol) of formic acid is added and stirring is continued at 50° C. for 1 hour. The reaction mixture is then cooled to room temperature, stirred for another hour and the solid phase is filtered off. The precipitated material is the salt formed between the levorotatory enantiomer of the starting material and L(+)-tartaric acid, in an optically slightly contaminated form. Weight: 30 g. Mp.: 167–169° C., after crystallization from ethanol. Racemization of this salt is described in examples II/4., 5., 6, 7 and 9. The mother liquor is evaporated in vacuo. The residue (≈29 g) is taken up in 200 ml of water and 200 ml of 1,2-dichloroethane and neutralized under stirring with 16 g (0,19 mol) of sodium hydrogen carbonate. The phases are separated, the aqueous layer is washed with 2×30 ml of 1,2-dichloroethane, the combined organic layer is extracted with 50 ml of water, dried over anhydrous sodium sulfate and evaporated in vacuo. Weight: 18 g. The raw product is recrystallized from 70 ml of ethanol, washed with a small amount of ethanol and dried. Weight: 12.6 g. Mp.: 122–124° C., $[\alpha]^{22}_D$=+69° (c=1, methanol). Yield: 66,3% calculated on the dextrorotatory enantiomer content of the starting material.

Optical purity: 99–100%, usually higher than 98% (determined by HPLC). The product was identified by elementary analysis, IR spectrum and $^1$H-NMR investigation. By concentration of the filtrate 4 g of racemic starting material can be recovered.

Example 9
Dextrorotatory [2-(2-Thienyl)ethylamino](2-chlorophenyl) acetamide 3.8 g (0.0129 mol) of racemic [2-(2-thienyl)ethylamino] (2-chlorophenyl)acetamide is dissolved at 50° C. in 38 ml of isopropanol and to this solution is added the 50° C. solution of 1.06 g (0.0071 mol) of D(−)-tartaric acid in 23 ml of isopropanol. The mixture is stirred at 50° C. for 30 minutes. Thick, white precipitate is formed. To the mixture 0.22 ml of formic acid is added and stirring is continued at 50° C. for 30 minutes. The precipitated material, which is the salt formed between the dextrorotatory enantiomer of the starting material and D(−)-tartaric acid, is filtered off at 50° C. Weight: 2.5 g. Mp.: 167–169° C (crystallized from ethanol). Racemization of the levorotatory isomer remaining in the mother liquor is described in Examples II/1,2 and 3.

The 2.5 g raw product thus obtained is taken up in the mixture of 10 ml of water and 10 ml of 1,2-dichloroethane and neutralized under stirring with 0.4 g of sodium hydrogen carbonate. The phases are separated, the organic layer is dried over anhydrous sodium sulfate and evaporated. The residue is recrystallized from 5 ml of isopropanol.

Weight: 1.2 g. Mp.: 122–124° C., $[\alpha]^{22}_D$=+67°. Yield: 63.3% calculated on the dextrorotatory enantiomer content of the starting material. The quality of the product is identical to that of the product obtained in the previous example.

Example 10
Dextrorotatory Methyl [2-(2-Thienyl)ethylamino](2-chlorophenyl)acetate-hydrochloride In 40 ml of methanol under cooling 11.5 ml (0.215 mol) of 100% sulfuric acid is dissolved, the solution is heated under reflux conditions for 30 minutes, then after cooling to room temperature 12.4 g (0.042 mol) of dextrorotatory [2-(2-thienyl)ehylamino](2-chlorophenyl)acetamide is added and the mixture is heated under reflux for 6–7 hours, till the end of the reaction. Methanol is distilled off in vacuo, to the residue 75 ml of 1,2-dichloroethane and 75 ml of water are added, the mixture is shaken well and the phases are separated. The aqueous phase is extracted with 2×20 ml of 1,2-dichloroethane, the united organic phase is extracted with 50 ml of 5% sodium hydroxide solution then with 50 ml of water, dried over anhydrous sodium sulfate. The drying-material is filtered off and 1.5 g (0.041 mol) of dry hydrogen chloride gas is introduced under cooling into the solution. The precipitated crystalline product is filtered off, washed with 1,2-dichloroethane and dried.

Weight: 12.1 g, mp.: 185–186° C. (decomposition), $[\alpha]^{22}_D$=+107°. Yield: 83%. Optical purity: in general 99–100%. The product was identified by elementary analysis, IR spectrum and $^1$H-NMR investigation.

Example 11
(+)-(S)-(2-Chlorophenyl)(6,7-dihydro-4H-thieno[3,2-c] pyridin-5-yl)acetic Acid Methyl Ester Hydrochloride Salt 6 g (0,017 mol) of dextrorotatory methyl [2-(2-thienyl) ethylamino](2-chlorophenyl) acetate hydrochloride is suspended in 6,7 ml of 38% aqueous formaline solution and heated to 60° C. under stirring. The starting material dissolves at 60° C., the resulting solution is stirred at that temperature for 30 minutes, till the completion of the reaction. The reaction mixture is then diluted with 100 ml of 1,2 dichloroethane and 150 ml of water, and after shaking well, the phases are separated. The aqueous phase is extracted with 2×30 ml of 1,2-dichloroethane, the united organic phase is extracted with 100 ml of water, dried over anhydrous sodium sulfate, filtered and evaporated in vacuo. The residual 6 g of material is dissolved in 30 ml of diethyl ether, and 0.6 g of dry hydrogen chloride gas is introduced into the solution under cooling, at room temperature. The precipitated crystalline material is filtered off, washed with ether and dried. Weight: 5,5 g. Mp.: 130–132° C., $[\alpha]^{22}_D$=+60°.

Yield: 90,1%. Optical purity: 99% (by HPLC investigation).

Example 12
a) (+)-(2-Chlorophenyl)-(6,7-dihydro-4H-thieno[3,2-c] pyridin-5-yl)acetic Acid Methyl Ester (−)-Camphorsulfonic Acid Salt 32 g (0.0994 mol) of (2-chlorophenyl)(6,7-dihydro-4H-thieno[3,2-c]pyridin-5-yl)acetic acid methyl ester is dissolved in 150 ml of acetone and to the solution 9.95 g (0.0397 mol) of levorotatory 10-camphorsulfonic acid monohydrate is added. The homogenous reaction mixture is allowed to stay at room temperature. After 48 hours a few crystals appear. The mixture is concentrated by evaporation to 50 ml and allowed to stay at room temperature for 24 hours. The resulting crystals are filtered off, washed with acetone and dried. The crystals thus obtained are dissolved again in a very small amount (50 ml) of hot acetone and after cooling the crystals are filtered off, washed with acetone and dried. Thus the title compound is obtained.

Yield: 88%. Mp.: 165° C. $[\alpha]^{20}{}_D$=+24° (c=1.68 g/100 ml; methanol).

b) (+)-(2-Chlorophenyl)-(6,7-dihydro-4H-thieno[3,2-c] pyridin-5-yl)acetic Acid Methyl Ester To the suspension made of 200 g of (+)-(2-chlorophenyl) (6,7-dihydro-4H-thieno[3,2-c]pyridin-5-yl)acetic acid methyl ester (−)-camphorsulfonic acid salt and 800 ml of dichloromethane is added 800 ml of sodium hydrogene carbonate solution. After stirring the organic phase is separated by decantation. The (+)-(2-chlorophenyl)(6,7-dihydro-4H-thieno[3,2-c]pyridin-5-yl)acetic acid methyl ester is obtained as a solution in 800 ml of dichloromethane. The solution is dried over sodium sulfate and the solvent is removed in vacuo.

The (+)-(2-chlorophenyl)(6,7-dihydro-4H-thieno[3,2-c] pyridin-5-yl)acetic acid methyl ester is obtained in the form of colourless oil.

c) (+)-(2-Chlorophenyl)(6,7-dihydro-4H-thieno[3,2-c] pyridin-5-yl)acetic Acid Methyl Ester Hydrogen Sulfate Salt The residue obtained in the previous example is dissolved in 500 ml of ice-cold acetone and to this solution 20.7 ml of concentrated sulfuric acid (93.64%; density 1.83) is added dropwise. The resulting precipitate is separated by filtration, washed with 1000 ml of acetone and dried in a vacuum oven at 50° C. Thus 139 g of the title salt is obtained in the form of white crystals. Mp.: 184° C., $[\alpha]^{20}{}_D$=+55.1° (c=1.891 g/100 ml; methanol).

Examples for the Preparation of the Racemic Compounds of General Formula (VII) Starting from the Optically Active Levorotatory Compounds of General Formula (VII) Obtained in Examples 8 and 9.

Example 13

29.5 g (0.1 mol) of R-(−)-[2-(2-thienyl)ethylamino](2-chlorophenyl)acetamide is dissolved at 60° C. in 120 ml of i-propanol, to the solution 0.8 g (0.02 mol) of sodium hydroxide is added. The mixture is stirred at 60° C. for 20 minutes then it is neutralised with 1.2 ml of acetic acid and concentrated in vacuo to half of its volume. The solution thus obtained is diluted with 200 ml of water, the resulting crystalline product is filtered off, washed with water and dried.

Product: racemic [2-(2-thienyl)ethylamino](2-chlorophenyl)acetamide, weight: 28,6 g (97%), mp: 90–92° C. IR (KBr), cm$^{-1}$: 3258, 2862, 1685, 1474, 1445, 1430, 1403, 1387, 1301, 1273, 1247, 1113, 1083, 1049, 1034, 938, 814, 752, 699, 602;

Example 14

29,5 g (0,1 mol) R-(−)-[2-(2-thienyl)ethylamino](2-chlorophenyl)acetamide is dissolved at 60° C. in 120 ml of ethanol, to the solution 0.56 g (0.01 mol) of potassium hydroxide is added. The mixture is stirred at 60° C. for 30 minutes, then it is neutralized with 0.6 ml of acetic acid and concentrated in vacuo to half of its volume. The solution thus obtained is diluted with 200 ml of water, the resulting crystalline product is filtered off, washed with water and dried.

Product: 28,6 g (97%), mp: 90–92° C. The product is identical with that of the above Example 13.

Example 15

29,5 g (0,1 mol) R-(−)-[2-(2-thienyl)ethylamino](2-chlorophenyl)acetamide is dissolved at 60° C. in 120 ml of ethanol, to the solution 2.1 g (0.03 mol) of sodium ethylate is added. The mixture is stirred at 60° C. for 30 minutes, then it is neutralized at 40–50° C. with 1.8 ml of acetic acid and concentrated in vacuo to half of its volume. The solution thus obtained is diluted with 200 ml of water, the precipitated crystalline product is filtered off, washed with water and dried.

Product: 28 g (95%), mp: 90–92° C. The product is identical with that of the above Example 13.

Example 16

44,5 g (0,1 mol) of R-(−)-[2-(2-thienyl)ethylamino](2-chlorophenyl)acetamide L(+)-tartarate is suspended in 250 ml of i-propanol. To the mixture 10 g (0.25 mol) of sodium hydroxide is added, it is stirred at 60° C. for 30 minutes, then it is neutralized at 40–50° C. with 3 ml of acetic acid. The main bulk of the solvent is distilled off in vacuo, the residue is diluted with 300 ml of water, the precipitated crystalline product is filtered off, washed with water and dried.

Product: 28,6 g (97%), mp: 90–92° C. The product is identical with that of the above Example 13.

Example 17

The procedure as described in Example 16. is followed, but after the end of the reaction and neutralization with acetic acid the resulting L(+) tartaric acid di-sodium salt and sodium acetate are removed by filtration at 60° C. The filtrate is then evaporated in vacuo, giving the product of the same amount and quality as described in Example 16.

Example 18

44.5 g (0.1 mol) of R-(−)-[2-(2-thienyl)ethylamino](2-chlorophenyl)acetamide L(+)-tartarate is suspended in 120 ml of ethanol, to it is added the solution of 20 g (0.5 mol) of sodium hydroxide in 120 ml of water. The mixture is stirred at 50° C. for 1 hour, the pH is then adjusted to 6.5 by the addition of 10% aqueous hydrochloric acid solution and cooled to room temperature. The resulting crystalline product is filtered off, washed with water and dried.

Product: 26,5 g (90%). The product is identical with that of the above Example 13.

Example 19

44.5 g (0.1 mol) of R-(−)-[2-(2-thienyl)ethylamino](2-chlorophenyl)acetamide L(+)-tartarate is suspended in 600 ml of benzene, to it are added 28 g (0.5 mol) of potassium hydroxide, 72 ml of water and 3 g of tetrabutylammonium bromide. The resulting two-phase mixture is heated under reflux for 1 hour, then, after cooling it to room temperature, it is diluted with 500 ml of water. The phases are separated, the aqueous layer is extracted with 2×100 ml of benzene. The united organic phase is washed with 2×150 ml of water, dried over anhydrous sodium sulfate, treated with fuller earth, filtered and evaporated in vacuo. The residue is suspended in 100 ml of ethanol, diluted with 400 ml of water, the crystalline product is filtered off, washed with water and dried.

Product: 28,6 g (97%), op: 90–92° C.

Example 20

33.1 g (0.1 mol) of S-(+)-[2-(2-thienyl)ethylamino](2-chlorophenyl)acetamide hydrochloride is suspended 120 ml of ethanol, to the mixture 6.2 g (0.11 mol) of potassium hydroxide is added, it is stirred at 60° C. for 30 minutes, then it is neutralized at 40–50° C. with 0.6 g of acetic acid, and concentrated in vacuo to half of its amount. The solution thus obtained is diluted with 200 ml of water, the resulting crystalline product is filtered off, washed with water and dried.

Product: 28,6 g (97%). Identification: as described in Example 13.

Example 21

44.5 g (0.1 mol) of R-(−)-[2-(2-thienyl)ethylamino](2-chlorophenyl)acetamide L(+)-tartarate is suspended in 220 ml of toluene, to it are added 22.4 g (0.4 mol) of potassium hydroxide, 60 ml of water and 1 g of tetrabutylammonium bromide. The resulting two-phase mixture is stirred at 70° C. for 30 minutes, cooled to room temperature, and the phases are separated. The aqueous layer is extracted with 60 ml of toluene, the united organic phases are washed with 2×50 ml of water and evaporated in vacuo. The residue is recrystallized from 40 ml of i-propanol. The product is filtered off at 0° C., washed with 40 ml of i-propanol, dried at 40–60° C.

Product: 28,6 g (97%), mp: 90–92° C.

What is claimed is:

1. A process for the racemization of the optically active compound of formula (VII) wherein X is halogen

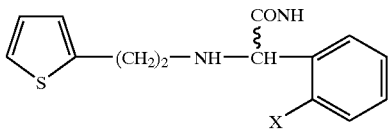
(VII)

which comprises reacting said compound or an acid addition salt thereof with an organic or inorganic base at a temperature between 40° C. and 60° C. in an organic solvent containing from 12–100% water.

2. A process according to claim 1 wherein the inorganic base is an alkali metal hydroxide.

3. A process according to claim 1 wherein the organic base is an alkali metal alcoholate.

4. A process according to claim 1 wherein an acid addition salt of a levorotatory compound of formula (VII) is reacted with an organic or inorganic base.

5. A process according to claim 1 wherein an acid addition salt of a dextrorotatory compound of formula (VII) is reacted with an organic or inorganic base.

6. A process according to claim 1 wherein the organic or inorganic base is used in an amount of 5–500 mol %, based on the levorotatory compound of formula (VII).

7. A process according to claim 1 wherein the organic or inorganic base is used in an amount of 5–500 mol %, based on the dextrorotatory compound of formula (VII).

8. A process according to claim 1 wherein the compond of formula VII is a mixture of the levorotatory and dextrorotatory compounds.

9. A process according to claim 1 wherein the mole ratio of the base to the compound of formula (VII) is from 1:3.5 to 1:0.2.

10. A process according to claim 9 wherein the reaction is carried out over a period of about 20–30 minutes.

* * * * *